(12) United States Patent (10) Patent No.: US 12,629,222 B2

Hu et al. (45) Date of Patent: May 19, 2026

(54) ROBOTIC SURGERY DEVICE AND FEEDING SYSTEM

(71) Applicant: Precision Robotics (Hong Kong) Limited, Shatin (HK)

(72) Inventors: Yang Hu, Shatin (HK); Ping Lai Benny Lo, Shatin (HK); Ho Fai Ma, Shatin (HK)

(73) Assignee: Precision Robotics (Hong Kong) Limited, Shatin (HK)

( * ) Notice: Subject to any disclaimer, the term of this patent is extended or adjusted under 35 U.S.C. 154(b) by 359 days.

(21) Appl. No.: 18/564,516

(22) PCT Filed: Apr. 13, 2022

(86) PCT No.: PCT/CN2022/086498

§ 371 (c)(1),
(2) Date: Nov. 27, 2023

(87) PCT Pub. No.: WO2022/247504

PCT Pub. Date: Dec. 1, 2022

(65) Prior Publication Data

US 2024/0261040 A1 Aug. 8, 2024

(30) Foreign Application Priority Data

May 26, 2021 (HK) ............................ 22021031822.0

(51) Int. Cl.
*A61B 34/30* (2016.01)
(52) U.S. Cl.
CPC ........ *A61B 34/30* (2016.02); *A61B 2034/301* (2016.02); *A61B 2034/303* (2016.02)
(58) Field of Classification Search
CPC .............. A61B 1/00133; A61B 1/0016; A61B 2034/301; A61B 2034/303; A61B 34/30; A61B 34/71
See application file for complete search history.

(56) References Cited

U.S. PATENT DOCUMENTS

| | | | |
|---|---|---|---|
| 2010/0204646 A1 | 8/2010 | Plicchi et al. | |
| 2013/0123580 A1* | 5/2013 | Peters ................. | A61B 1/0016 |
| | | | 604/95.04 |

(Continued)

FOREIGN PATENT DOCUMENTS

| | | |
|---|---|---|
| CN | 103536367 A | 1/2014 |
| CN | 108309370 A | 7/2018 |

(Continued)

OTHER PUBLICATIONS

International Search Report from PCT International Application No. PCT/CN2022/086498 dated Jul. 3, 2022.

(Continued)

*Primary Examiner* — Scott Luan

(74) *Attorney, Agent, or Firm* — Budzyn IP Law, LLC

(57) ABSTRACT

A robotic surgery device and a feeding system, the robotic surgery device is in communication with a feeding device for tubular component, and includes a synchronous rotary means, including a bracket, a rotary stage, a rotary motor and a rotation transmitting member, wherein the rotary stage is rotatably arranged over the bracket; the tubular component is drawn out from the feeding device and then connected to the rotary stage; as the tubular component rotates when driven by the feeding device, the rotary motor drives the rotary stage to rotate synchronously via the rotation transmitting member; and a synchronous translating means connected with the synchronous rotary means, wherein as the tubular component moves back and forth when driven by the feeding device, the synchronous translating means moves in coordination with the tubular component. Compared with prior art, the robotic surgery device can free the operator's hands and reduce the use costs.

10 Claims, 5 Drawing Sheets

(56)                    References Cited

U.S. PATENT DOCUMENTS

| | | | |
|---|---|---|---|
| 2014/0296637 A1 | 10/2014 | Lee et al. | |
| 2019/0351187 A1 | 11/2019 | Choi et al. | |

FOREIGN PATENT DOCUMENTS

| | | |
|---|---|---|
| CN | 207821903 U | 9/2018 |
| CN | 110151310 A | 8/2019 |
| CN | 210056225 U | 2/2020 |
| CN | 211024680 U | 7/2020 |
| CN | 112168309 A | 1/2021 |

OTHER PUBLICATIONS

Written Opinion from International Application No. PCT/CN2022/086498 dated Jul. 4, 2022.

* cited by examiner

ROBOTIC SURGERY DEVICE AND FEEDING SYSTEM

CROSS-REFERENCE TO RELATED APPLICATIONS

This Application is a National Stage Application under 35 U.S.C. § 371 of PCT Application No. PCT/CN2022/086498, filed Apr. 13, 2022 which claims priority to Hong Kong Patent Application No. 22021031822.0, filed May 26, 2021, the entire contents of which are incorporated by reference herein.

TECHNICAL FIELD

The present application to the technical field of conveying a tubular object, more particular to a robotic surgery system and a robotic surgery device applied in the system.

BACKGROUND OF THE INVENTION

In various applications, it is often necessary to explore the inside of a pipe-shaped object (also referred to as a "pipe"). In addition to observing the inside of the pipe to find out defects and flaw, sometimes it is also necessary to repair such defects and flaw.

To avoid additional damage to the pipe and some external structures attached thereto during the process of flaw detection or repair, various tools (e.g., cameras) are typically installed on a tubular component. With the tubular component having been inserted into the pipe from one end thereof, internal structures of the pipe can be explored and repaired. In this case, insertion of the tubular component usually relies on a feeding mechanism for tubular component, besides normal manual operations.

The present application is useful in various types of pipes, such as internal cavities of human body, besides industrial pipes. Tubular components applicable to internal cavities of human body may be an endoscope or a single-port surgical manipulator. As for straight pipes, feeding of tubular components is very convenient. However, as for pipes with many bends or bifurcations, or pipes with a flexible wall, tubular components need to possess a bendable or flexible characteristic, and feeding of such tubular components is not so easy.

SUMMARY OF THE INVENTION

In order to solve or at least partly solve the aforementioned technical problems, the present application provides a robotic surgery device in communication with a feeding device for tubular component, comprising: a synchronous rotary means including a bracket, a rotary stage, a rotary motor and a rotation transmitting member, wherein the rotary stage is rotatably arranged over the bracket; the tubular component is drawn out from the feeding device and then connected to the rotary stage; as the tubular component rotates when driven by the feeding device, the rotary motor drives the rotary stage to rotate synchronously via the rotation transmitting member; and a synchronous translating means connected with the synchronous rotary means, wherein as the tubular component moves back and forth when driven by the feeding device, the synchronous translating means moves in coordination with the tubular component.

The present application also provides a robotic surgery system, comprising a feeding device for tubular component and the above-mentioned robotic surgery device, wherein the feeding device is in communication with the robotic surgery device, and as the tubular component moves when driven by the feeding device, the robotic surgery device drives the tubular component to move synchronously.

Compared with the prior art, the robotic surgery device of the present application can make the tubular component rotate and translate, by the provision of a synchronous rotary means and a synchronous translating means, thereby ensuring the freedom of motion of the tubular component. With the robotic surgery device being in communication with the feeding device for tubular component, the robotic surgery device and the feeding device can be synchronized to perform a coordinated movement. As a result, the entire feeding process will only require automatic operation of mechanical equipment, which can free the operator's hands and reduce the use costs.

BRIEF DESCRIPTION OF THE DRAWINGS

To better explain embodiments of the present application, relevant drawings will be briefly described below. It is understood that, drawings described below are only used to illustrate certain embodiments of the application, and those of ordinary skill in the art could perceive many other technical features and connections that are not mentioned herein, based on these drawings.

REFERENCE SIGNS 1. robotic surgery device; 11. synchronous rotary means; 111. bracket; 1111. support seat; 1112. support ring; 1113. transmission opening; 112. rotary stage; 1121. rotary drum; 1122. extended platform; 113. rotary motor; 114. rotation transmitting member; 12. synchronous translating means; 121. first slide; 122. first power source; 123. first guide rail; 125. second slide; 126. second power source; 127. second guide rail; 128. base; 129. revolving belt; 13. first traction means; 14. second traction means; 2. feeding device; 3. tubular component.

DETAILED DESCRIPTION OF EMBODIMENTS

The present application will be described in detail below with reference to drawings.

Figure 1:
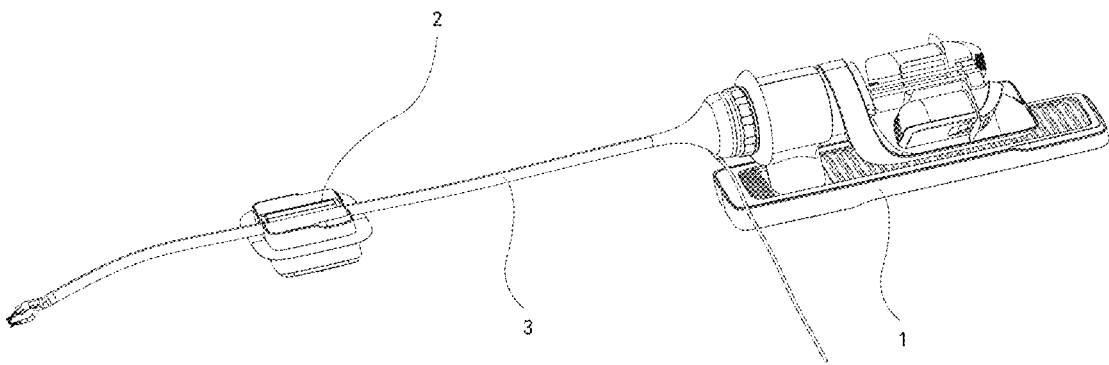
FIG. 1 is a schematic view of a robotic surgery system.

A robotic surgery system according to the present application is schematically shown in FIG. 1, comprising a feeding device 2 for tubular component, and a robotic surgery device 1.

As shown, a front section of a tubular component 3 is clamped by the feeding device 2, and moves back and forth, or rotates about its own axis, when driven by the feeding device 2. A rear section of the tubular component 3 is connected to the robotic surgery device 1 arranged behind the feeding device 2. Through a communication between the feeding device 2 and the robotic surgery device 1, the robotic surgery device 1 enables a coordinated movement of the tubular component 3, as the tubular component 3 moves when driven by the feeding device 2.

The feeding device 2 for tubular component can be any of well-known devices in the prior art, so long as it is capable of feeding the tubular component 3. The robotic surgery device 1 serves to allow for a synchronous movement of the rear section of the tubular component 3. As auxiliary traveling equipment for the tubular component 3, the robotic surgery device 1 is usually used in conjunction with the feeding device 2 when the tubular component 3 is a flexible hose, and can also be used independently when the tubular component 3 is a rigid tube.

Specifically, the robotic surgery device 1 may communicate with the feeding device 2, and referring to FIGS. 2 to 6, comprises a synchronous rotary means 11 and a synchronous translating means 12 connected with the synchronous rotary means 11. The synchronous rotary means 11 includes a bracket 111, a rotary stage 112, a rotary motor 113 and a rotation transmitting member 114. The rotary stage 112 is rotatably arranged over the bracket 111. The tubular component 3 is drawn out from the feeding device 2 and is then connected to the rotary stage 112. The tubular component 3 is driven by the feeding device 2 to rotate, while the rotary motor 113 drives the rotary stage 112 to rotate synchronously over the bracket 111 by means of the rotation transmitting member 114. As the tubular component 3 moves back and forth when driven by the feeding device 2, the synchronous translating means 12 can move in coordination with the tubular component 3.

Figure 2:
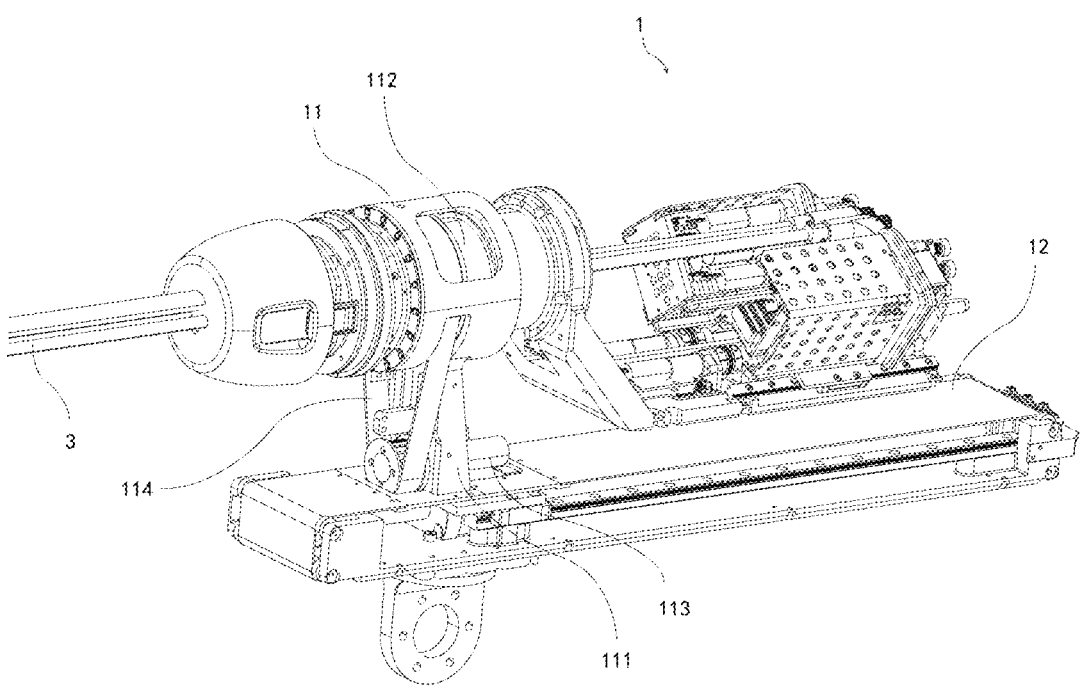
FIG. 2 is a schematic structural view of a robotic surgery device.

The rotation transmitting member 114 may be of a belt transmission structure as shown in FIG. 2, and also may be of a gear or a sprocket transmission structure, so long as it can drive the rotary stage 112 to rotate stably.

The tubular component 3, due to its elongated shape, usually possesses a center of gravity far away from its end, and thus an insufficient rigidity. As a result, when the tubular component 3 is supported at a mid-point, unsupported ends of the tubular component 3 are prone to sagging or deformation. To guarantee the accuracy of feeding, the feeding device 2 is usually disposed at an entrance of a pipe to be entered. In this case, as shown in FIG. 1, one end of the tubular component 3 is clamped by the feeding device 2. If there is no support at the other end, it would be difficult to perform accurate feeding operation while maintaining an original shape of the tubular component 3. Further, if the tubular component 3 is made of a flexible material, this problem will become more prominent. Especially for a feeding mechanism required for rotating the tubular component 3, while the feeding mechanism drives the tubular component 3 to rotate, the flexible component would be easily twisted, which makes the feeding operation difficult. As a result of this problem, the feeding of a tubular component in the prior art usually requires auxiliary manual operations, which are rather complicated and costly.

In contrast, by providing a synchronous rotary means 11 and a synchronous translating means 12 as in the present application, the robotic surgery device 1 enables the tubular component 3 to rotate and to translate back and forth, and the freedom of motion of the tubular component 3 is thus guaranteed. With the robotic surgery device 1 being in communication with the feeding device 2, the robotic surgery device 1 and feeding device 2 can be synchronized to perform a coordinated movement. As such, the entire feeding process only requires automatic operation of mechanical equipment, and therefore can free the operator's hands and reduce the use costs.

Figure 3:
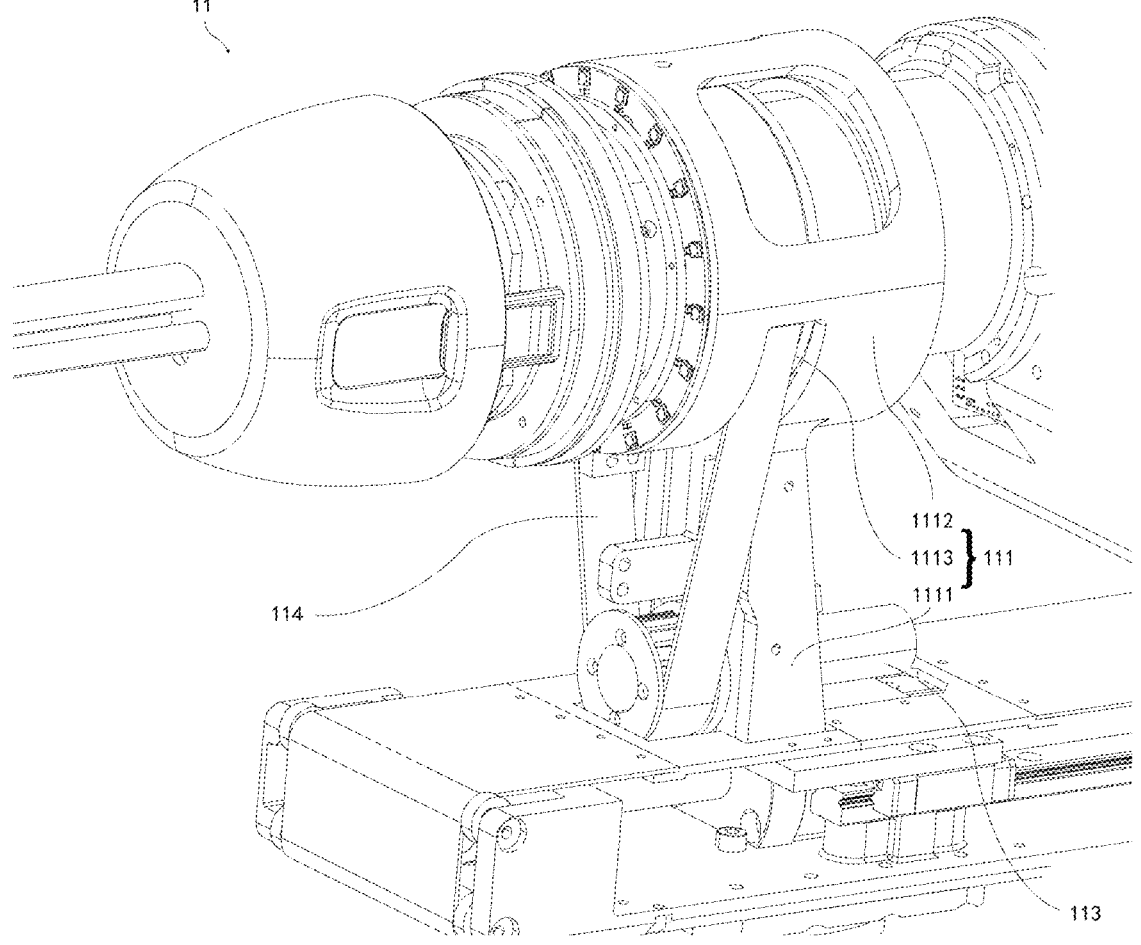
FIG. 3 is a partial structural view of the robotic surgery device near a synchronous rotary means.

In an embodiment of the synchronous rotary means 11 as shown in FIGS. 2 and 3, the bracket 111 may include a support base 1111 and a support ring 1112 fixed to the support base 1111. The rotary stage 112 is fitted within the support ring 1112, and is rotatable relative to the support ring 1112. The rotary motor 113 may be mounted to the bracket 111 so as to make the rotary motion of the synchronous rotary means 11 more stable. The support ring 1112 may be configured in a sleeve shape, and bearing(s) may be provided on an inner wall of the support ring 1112, so as to better support the rotary stage 112 and to facilitate rotation of the rotary stage 112 with low resistance. Optionally, the support ring 1112 may be further formed with a transmission opening 1113. The rotation transmitting member 114 passes through the support ring 1112 through the transmission opening 1113, and is then drivingly connected to the rotary stage 112. The rotation transmitting member 114 drives the rotary stage 112 to rotate through the transmission opening 1113 formed in the support ring 1112, so that the force driving the rotary stage 112 to rotate acts on the rotary stage 112 more evenly, leading to better force stability.

Figure 4:
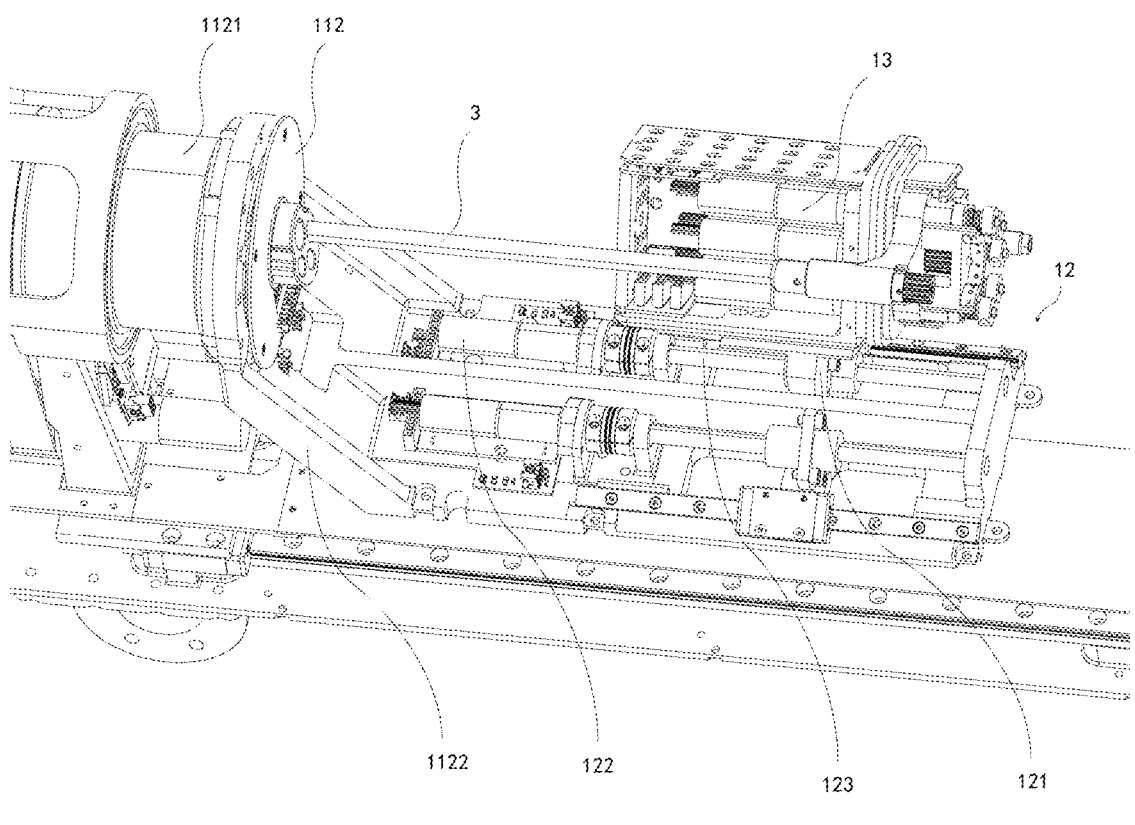
FIG. 4 is a partial structural view of the robotic surgery device near an extended platform.

In an embodiment as shown in FIG. 4, the synchronous translating means 12 may include a first slide 121, a first power source 122 and a first guide rail 123, wherein the first slide 121 is arranged on the first guide rail 123. The first guide rail 123 is mounted to the rotary stage 112 and extends along the extension direction of the tubular component 3. The tubular component 3 is drawn out from the rotary stage 112 and then connected to the first slide 121. As the tubular component 3 moves back and forth when driven by the feeding device 2, the first power source 122 can drive the first slide 121 to move synchronously along the first guide rail 123. Thus, when the rotary stage 112 rotates, the first slide 121 and the first power source 122 associated with the first guide rail 123 will also rotate, since the first guide rail 123 is mounted to the rotary stage 112. On the other hand, when the feeding device 2 drives the tubular component 3 to move back and forth, the first power source 122 can also drive the tubular component 3 to follow this back and forth movement, with the aid of a synchronization signal.

The rotary stage 112 may include a rotary drum 1121 which is supported by the bracket 111 and is rotatable relative to the bracket 111, and an extended platform 1122 connected to an end of the rotary drum 1121 away from the feeding device 2. The first guide rail 123 is mounted to the extended platform 1122. In case the first rail 123 is mounted to the extended platform 1122, the extended platform 1122 can provide sufficient installation space for the first rail 123, ensuring that the rotations of the rotary drum 1121, the extended platform 1122 and even the first slide 121 are all synchronized, and the stability of the feeding system is very excellent.

Referring to FIG. 4, the first power source 122 may be a motor, and the first guide rail 123 may be a motor shaft of the first power source 122. In this case, a lead screw structure, which is highly simplified and reliable, is formed between the first guide rail 123 and the first slide 121. Of course, the first power source 122 may alternatively render a linear movement of the first slide 121 by means of a rack-pinion structure, or a worm-gear structure.

Optionally, when the tubular component 3 is an endoscope, the robotic surgery device 1 may further include a first traction means 13 for drive cables of the endoscope, which is mounted to the first slide 121. A conventional endoscope usually has multiple drive cables to control bending of multistage sheaths of the endoscope in multiple degrees of freedom. Correspondingly, the first traction means 13 may include a plurality of motors for tracking these drive cables respectively. By mounting a driving means for the endoscope to the first slide 121, the movement of the tubular component 3 will not affect operation of drive cables of the endoscope, and the working stability of the endoscope will be improved.

Figure 5:
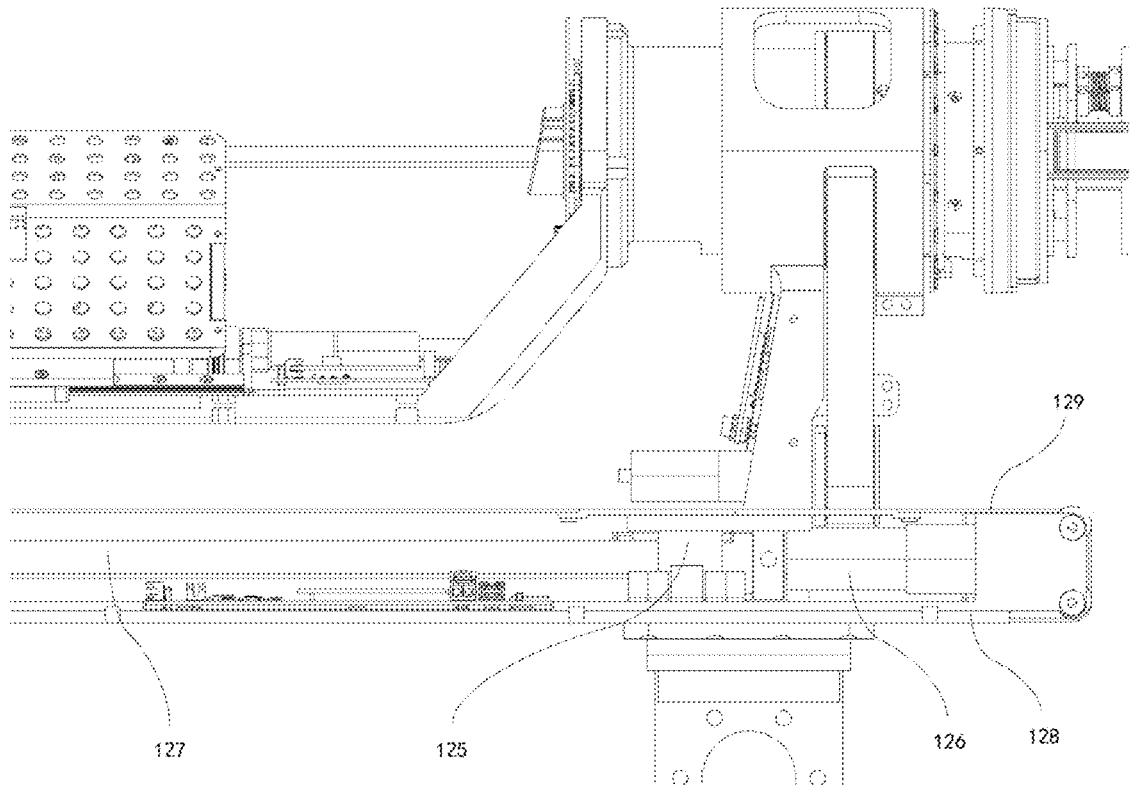
FIG. 5 is a partial structural view of another robotic surgery device near a base.

In addition to the above-mentioned synchronous translating means 12, another synchronous translating means 12 is provided in the present application. As shown in FIG. 5, the synchronous translating means 12 may include a second slide 125, a second power source 126 and a second guide rail 127, wherein the second slide 125 is arranged on the second guide rail 127. The bracket 111 is mounted to the second slide 125, and the second guide rail 127 extends along the extension direction of the tubular component 3. As the tubular component 3 moves back and forth when driven by the feeding device 2, the second power source 126 can drive the second slide 125 to move synchronously along the second guide rail 127. As the bracket 111 is mounted to the second slide 125, the bracket 111 along with the entire synchronous rotary means 11 provided at the bracket 111 can be driven to move back and forth. In this case, if the feeding device 2 drives the tubular component 3 to move back and forth, the second power source 126 will drive the tubular component 3 to follow this back and forth movement, with the aid of a synchronization signal. It is understood that the second power source 126 may also employ various mechanical transmission structures converting a rotary movement into translation, such as a lead screw, a rack-pinion, a worm-gear, etc., so that the second slide 125 can move back and forth synchronously.

Optionally, referring to FIG. 5, the synchronous translating means 12 may include a base 128, within which the second guide rail 127 and the second slide 125 are disposed, and a revolving belt 129 arranged around the base 128. The revolving belt 129 is provided with an opening, through which the bracket 111 passes and is then connected to the second slide 125. While the second slide 125 moves along the second guide rail 127, the revolving belt 129 is driven to revolve. Since the second guide rail 127 and the second slide 125 are disposed within the base 128, an elongated slot needs to be formed in the base 128, so as to allow for back and forth movement of the bracket 111. The revolving belt 129 covers the elongated slot, and serves to prevent ingress of dust and water, etc. That is, when the bracket 111 moves back and forth along the elongated slot in the base 128, the revolving belt 129 would moves synchronously, so that the bracket 111 always passes through a part of the elongated slot and the opening in the revolving belt 129, while the revolving belt 129 covers the rest of the elongated slot.

In the present application, two types of synchronous translating means 12 as described can be used independently or simultaneously. Compared with the solution in which the first rail 123 and the first slide 121 are mounted to the rotary stage 112, in the solution where the second rail 127 and the second slide 125 are disposed within the base 128, the installation space will not be affected by the shape of the rotary stage 112. Accordingly, the latter allows for a longer stroke, and is therefore more suitable for use in positioning the tubular component 3. In contrast, compared with the solution in which the second guide rail 127 and the second slide 125 are disposed within the base 128, in the solution where the first guide rail 123 and the first slide 121 are mounted to the rotary stage 112, it is unnecessary to move the rotary stage 112 at the time of adjustment, and there are fewer linkage structures. Accordingly, the latter can perform more precise positioning operation, and is therefore more suitable in case the tubular component 3 is intended for precise operations. If the two synchronous means are combined, those advantages of the two will be superimposed, so the robotic surgery device 1 can allow for a coordinated movement of the feeding device 2 in a more cooperative and adaptive way.

Figure 6:
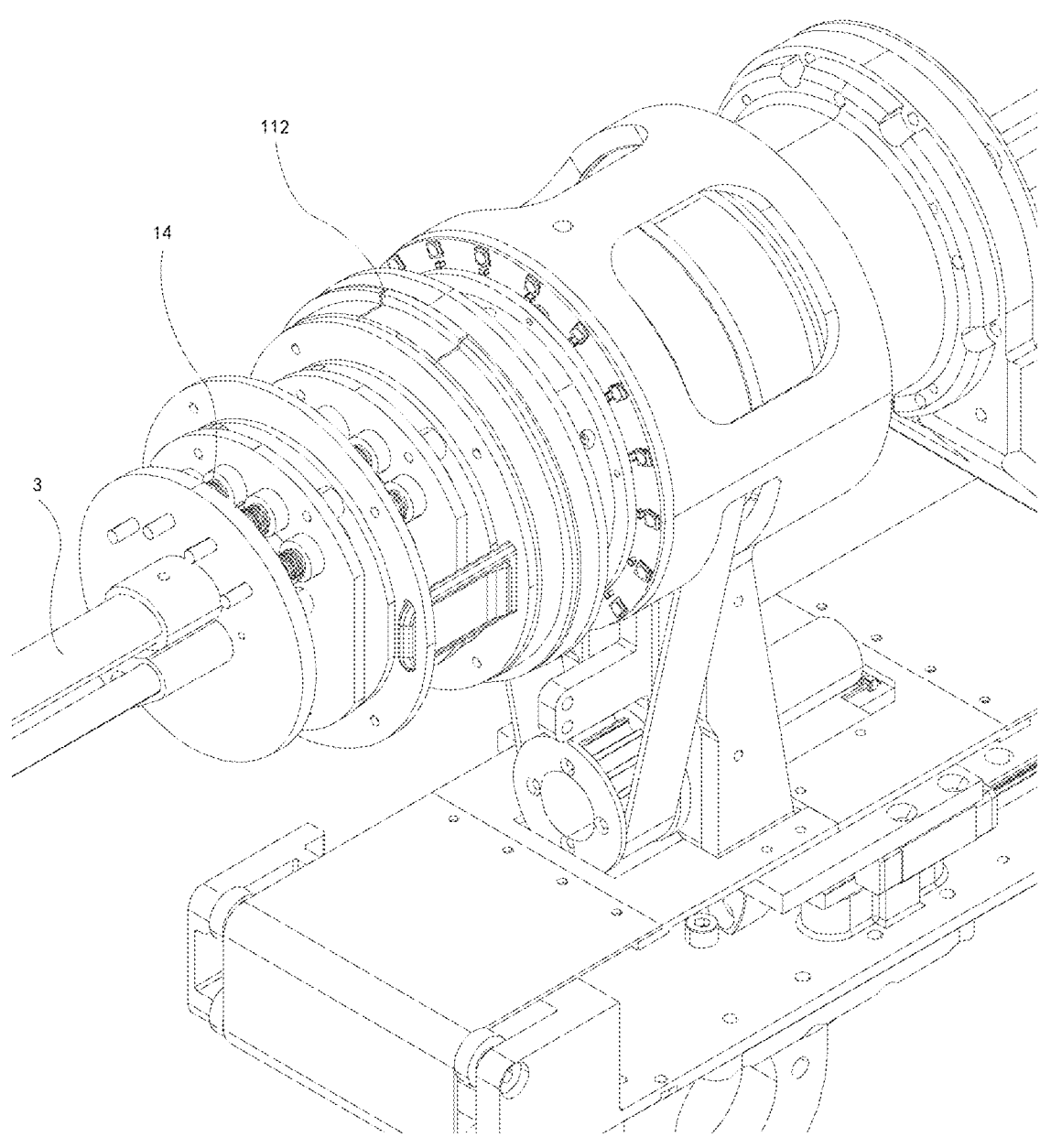
FIG. 6 is a partial structural view of another robotic surgery device near a rotary stage.

Additionally, certain tubular components 3 in an endoscope do not require precise operations, such as negative pressure pipes only used to extract gas or liquid, or lamp pipes for lighting only. For such tubular components 3, the robotic surgery device 1 may have a second traction means 14 for drive cables of the endoscope, which is mounted to the rotary stage 112, as shown in FIG. 6. In this case, connecting drive cables directly to the rotary stage 112 can significantly simplify the structure and reduce the cost of the feeding system.

While the present application has been described in detail with reference to only a limited number of embodiments, it is understood that the application is not limited to such disclosed embodiments. Rather, the application can be modified to incorporate any number of variations, alterations, substitutions or equivalent arrangements which are heretofore not described, but are commensurate with the spirit and scope of the application. Further, while various embodiments of the application have been described, it is understood that each aspect of the application may include only some of the described embodiments. Generally, the application is not limited by the foregoing description, but is only limited by the scope of the appended claims.

What is claimed is:

1. A robotic surgery device in communication with a feeding device for tubular component, comprising:
   a synchronous rotary means including a bracket, a rotary stage, a rotary motor and a rotation transmitting member, wherein the rotary stage is rotatably arranged over the bracket; the tubular component is drawn out from the feeding device and then connected to the rotary stage; as the tubular component rotates when driven by the feeding device, the rotary motor drives the rotary stage to rotate synchronously via the rotation transmitting member; and
   a synchronous translating means connected with the synchronous rotary means, wherein as the tubular component moves back and forth when driven by the feeding device, the synchronous translating means moves in coordination with the tubular component.

2. The robotic surgery device according to claim 1, wherein the bracket comprises a support seat and a support ring fixed to the support seat, wherein the rotary stage is fitted within the support ring and is rotatable relative to the support ring.

3. The robotic surgery device according to claim 2, wherein the support ring is formed with a transmission opening, the rotation transmitting member passing through the transmission opening and being drivingly connected to the rotary stage.

4. The robotic surgery device according to claim 1, wherein the synchronous translating means comprises a first slide, a first power source, and a first guide rail on which the first slide is arranged;
   wherein, the first guide rail is mounted to the rotary stage along the extension direction of the tubular component;
   the tubular component is drawn out from the rotary stage and then connected to the first slide;

as the tubular component moves back and forth when driven by the feeding device, the first power source drives the first slide to move synchronously along the first guide rail.

5. The robotic surgery device according to claim 4, wherein the tubular component is an endoscope; the robotic surgery device further comprises a first traction means for drive cables of the endoscope, which is mounted to the first slide.

6. The robotic surgery device according to claim 4, wherein the rotary stage comprises:

a rotary drum supported by the bracket and rotatable relative to the bracket; and an extended platform connected to an end of the rotating drum far away from the feeding device, to which the first guide rail is mounted.

7. The robotic surgery device according to claim 1, wherein the synchronous translating means comprises a second slide, a second power source, and a second guide rail on which the second slide is arranged;

wherein, the bracket is mounted to the second slide, and the second guide rail extends along the extension direction of the tubular component;

as the tubular component moves back and forth when driven by the feeding device, the second power source drives the second slide to move synchronously along the second guide rail.

8. The robotic surgery device according to claim 7, wherein the synchronous translating means further comprises:

a base, within which the second guide rail and the second slide are disposed; and a revolving belt arranged around the base and formed with an opening, the bracket passing through the opening and being connected to the second slide;

wherein, while the second slide moves, the revolving belt is driven to revolve.

9. The robotic surgery device according to claim 1, wherein the tubular component is an endoscope; the robotic surgery device further comprises a second traction means for drive cables of the endoscope, which is mounted to the rotary stage.

10. A robotic surgery system, comprising a feeding device for tubular component and the robotic surgery device according to claim 1, wherein the feeding device is in communication with the robotic surgery device, and as the tubular component moves when driven by the feeding device, the robotic surgery device drives the tubular component to move synchronously.

* * * * *